US008414889B2

(12) United States Patent  
Cassone et al.

(10) Patent No.: US 8,414,889 B2  
(45) Date of Patent: Apr. 9, 2013

(54) PROTECTIVE ANTI-GLUCAN ANTIBODIES WITH PREFERENCE FOR β-1,3-GLUCANS

(75) Inventors: Antonio Cassone, Rome (IT); Antonella Torosantucci, Rome (IT)

(73) Assignees: Antonio Cassone, Rome (IT); Antonella Torosantucci, Rome (IT)

( * ) Notice: Subject to any disclaimer, the term of this patent is extended or adjusted under 35 U.S.C. 154(b) by 0 days.

(21) Appl. No.: 13/331,032

(22) Filed: Dec. 20, 2011

(65) Prior Publication Data

US 2012/0107316 A1 May 3, 2012

Related U.S. Application Data

(60) Division of application No. 12/851,962, filed on Aug. 6, 2010, now Pat. No. 8,101,406, which is a continuation of application No. 11/662,880, filed as application No. PCT/IB2005/003153 on Sep. 14, 2005, now Pat. No. 7,893,219.

(30) Foreign Application Priority Data

Sep. 14, 2004 (GB) .................................. 0420466.5

(51) Int. Cl.  
*A61K 39/395* (2006.01)  
*A61K 39/40* (2006.01)

(52) U.S. Cl. ............... 424/137.1; 424/133.1; 424/135.1; 424/141.1; 424/142.1

(58) Field of Classification Search .................. None  
See application file for complete search history.

(56) References Cited

U.S. PATENT DOCUMENTS

| 5,306,492 | A | 4/1994 | Porro |
| 5,530,101 | A | 6/1996 | Queen et al. |
| 6,248,329 | B1 | 6/2001 | Chandrashekar et al. |
| 6,294,321 | B1 | 9/2001 | Wakshull et al. |
| 6,309,642 | B1 | 10/2001 | Cutler et al. |
| 7,601,351 | B1 | 10/2009 | Rosen et al. |
| 2007/0141088 | A1 | 6/2007 | Polonelli et al. |

FOREIGN PATENT DOCUMENTS

| JP | 63-83012 | 4/1988 |
| JP | 09-309842 | 12/1997 |
| WO | WO 96/28476 A1 | 9/1996 |
| WO | WO 99/31510 A | 6/1999 |
| WO | WO 99/55715 A2 | 11/1999 |
| WO | WO 03/097091 A | 11/2003 |
| WO | WO 2004/036222 A | 4/2004 |

OTHER PUBLICATIONS

Adachi, et al., "Preparation and Antigen Specificity of an Anti-(1->3)-Beta-D-Glucan Antibody," *Biological and Pharmaceutical Bulletin* 17(11):1508-1512 (1994).
Bromuro, et al., "Interplay Between Protective and Inhibitory Antibodies Dictates the Outcome of Experimentally Disseminated Candidiasis in Recipients of a *Candida abicans* Vaccine," *Infection and Immunity* 70(10):5462-5470 (2002).
Casadevall, et al., "Antibody Immunity and Invasive Fungal Infections," *Infection and Immunity* 63(11):4211-4218 (1995).
Casadevall, et al., "Antibody-Mediated Protection Through Cross-Reactivity Induces a Fungal Heresy Into Immunological Dogma," *Inf Immun* 7 5(11):5074-5078 (2007).
Deepe, "Prospects for the Development of Fungal Vaccines," *Clinical Microbiology Reviews* 10(4):585-596 (1997).
Derwent Abstract for "Method Produce Cell Wall Skeleton Powder Red Norcia," *Derwent Publications Ltd.*, London, GB, Class B04, One Page (1994) XP002264615.
Harlowe, et al., "Antibodies: A Laboratory Manual," *Cold Spring Harbor Laboratory* pp. 96-97 (1988).
Honey, "β-Glucan Conjugate Provides Protection," Nat Rev Immunol 4:814 (2005).
Kieber-Emmons, "Peptide Mimotopes of Carbohydrate Antigens," *Immunologic Research* 17(1-2):95-108 (1998).
Kieber-Emmons, et al., "Cutting Edge:DNA Immunization with Minigenes of Carbohydrate Mimotopes Induce Functional Anti-Carbohydrate Antibody Response," *Journal of Immunology* 165(2):623-627 (2000).
Kondori, et al., "*Candida albicans* Cell Wall Antigens for Serological Diagnosis of Candidemia," *Medical Mycology* 41(1):21-30 (2003).
Masuzawa, et al., "Solubilized *Candida* Cell Wall Beta-Glucan, CSBG, is an Epitope of Natural Human Antibody," *Drug Development Research* 58(2):179-189 (2003).
Miura, et al., "Antigen-Specific Response of Murine Immune System Toward a Yeast Beta-Glucan Preparation, Zymosan," *FEMS Immunol Med Microbiol* 24:131-139 (1999).
Ohno, et al., "Solubilization of Yeast Cell-Wall Beta-(1→3)-D-Glucan by Sodium Hypochlorite Oxidation and Dimethyl Sulfoxide Extraction," *Carbohydrate Res* 316:161-172 (1999).
Rachini, et al., "An Anti-B-Glucan Monoclonal Antibody Inhibits Growth and Capsule Formation of *Cryptococcus neoformans* in Vitro and Exerts Therapeutic, Anticryptococcal Activity in Vivo," *Inf Immun*_75(11):5085-5094 (2007).
Ross, et al., "Therapeutic Intervention With Complement and β-Glucan in Cancer," *Immunopharmacology* 42:61-74 (1999).
Sadamoto, et al., "Evidence for Interference by Immune Complexes in the Serodignosis of Cryptococcosis," *Microbiol Immunol* 37(2):129-133 (1993).
Tokunaka, et al., "Immunopharmacological and Immunotoxicological Activities of a Water-Soluble (1→3)-β-Glucan, CSBG From *Candida* spp," *Int J Immunopharm* 22:383-394 (2000).
Torosantucci, et al., "A Novel Glyco-Conjugate Vaccine Against Fungal Pathogens," *J Exp Med* 202(5):597-606 (2005).

(Continued)

*Primary Examiner* — Patricia A Duffy  
(74) *Attorney, Agent, or Firm* — Roberta L. Robins; Robins Law Group

(57) ABSTRACT

Anti-β-1,3-glucan antibodies have been found to be protective against systemic fungal infection with *Candida albicans*. The present invention provides monoclonal antibodies that bind to β-1,3-glucan, hybridoma cell lines producing the antibodies, compositions comprising the antibodies and methods of using such antibodies for treatment of microbial infections, particularly against *Candida albicans* and *Aspergillus fumigatis* infections. The antibodies of the present invention are not specific for β-1,6-glucan.

9 Claims, 6 Drawing Sheets

OTHER PUBLICATIONS

Torres-Bauza, et al., "Protoplasts From Yeast and Mycelial Forms of *Candida albicans*," *J Gen Microbiol* 119:341-349 (1980).

Tzianabos, "Polysaccharide Immunomodulators as Therapeutic Agents: Structural Aspects and Biological Function," *Clinical Microbiology Reviews* 13(4):523-533 (2000).

Tzianabos, et al., "Protection Against Experimental Intraabdominal Sepsis by Two Polysaccharide Immunomodulators," *J Infect Dis* 178:200-206 (1998).

Torosantucci, et al., "Protection by Anti-β-Glucan Antibodies is Associated with Restricted β-1,3 Glucan Binding Specificity and Inhibition of Fungal Growth and Adherence," *PLoS One* 4(4):e5392, pp. 1-17 (2009).

Bendig, Methods: A Companion to Methods in Enzymology 8:83-93 (1995).

Hirata, et al., "Monoclonal Antibody to Proteoglycan Derived From *Grifola frondosa* (Maitake)," *Biological & Pharmaceutical Bulletin (of Japan)*, Pharmaceutical Society of Japan 17(4):539-542 (1994).

Miekle, et al., "The Location of 1-3-Beta Glucans in the Walls of Pollen Tubes of *Nicotiana-alata* Using a 1-3-Beta Glucan-Specific Monoclonal Antibody," *Planta* 185(1):1-8 (1991)

Torosantucci, "A Novel Glyco-Conjugate Vaccine Against Fungal Pathogens," *J Exp Med* 202(5):597-606 (2005).

Jones, et al., Nature, 321:522-525 (1986).

Morrison et al., PNAS, 81:6851-6855 (1984).

Queen et al., PNAS, 86:10029-10033 (1989).

Morrison et al., Adv. Immunol., 44:65-92 (1989).

SEQUENCE LISTING

<160> NUMBER OF SEQ ID NOS: 14

<210> SEQ ID NO 1
<211> LENGTH: 121

```
<212> TYPE: PRT
<213> ORGANISM: Artificial Sequence
<220> FEATURE:
<223> OTHER INFORMATION: 2G8 Light chain variable region

<400> SEQUENCE: 1

Asp Ile Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Asn Thr His Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Phe Tyr Tyr Cys Val Gln Gly
                85                  90                  95

Thr His Phe Pro Tyr Thr Phe Gly Gly Gly Thr Lys Leu Glu Ile Lys
            100                 105                 110

Arg Ala Asp Ala Ala Pro Thr Val Ser
        115                 120

<210> SEQ ID NO 2
<211> LENGTH: 125
<212> TYPE: PRT
<213> ORGANISM: Artificial Sequence
<220> FEATURE:
<223> OTHER INFORMATION: 2G8 Heavy chain variable region

<400> SEQUENCE: 2

Leu Gln Gln Ser Gly Ala Glu Leu Met Lys Pro Gly Ala Ser Val Lys
1               5                   10                  15

Ile Ser Cys Lys Ala Thr Gly Tyr Thr Leu Ser Ser Tyr Trp Leu Glu
            20                  25                  30

Trp Val Lys Gln Arg Pro Gly His Gly Leu Glu Trp Ile Gly Glu Ile
        35                  40                  45

Leu Pro Gly Ser Gly Ser Thr Asn Tyr Asn Glu Lys Phe Lys Gly Lys
    50                  55                  60

Ala Thr Phe Thr Ala Asp Thr Ser Ser Asn Thr Ala Tyr Met Gln Leu
65                  70                  75                  80

Ser Ser Leu Thr Ser Glu Asp Ser Ala Val Tyr Tyr Cys Ala Arg Glu
                85                  90                  95

Gly Trp Tyr Phe Asp Val Trp Gly Ala Gly Thr Thr Val Thr Val Ser
            100                 105                 110

Ser Ala Lys Thr Thr Pro Pro Ser Val Tyr Pro Leu Ala
        115                 120                 125

<210> SEQ ID NO 3
<211> LENGTH: 24
<212> TYPE: DNA
<213> ORGANISM: Artificial Sequence
<220> FEATURE:
<223> OTHER INFORMATION: 2G8 Heavy chain CDR1

<400> SEQUENCE: 3
ggctacacac tcagtagcta ctgg                                          24

<210> SEQ ID NO 4
<211> LENGTH: 8
```

```
<212> TYPE: PRT
<213> ORGANISM: Artificial Sequence
<220> FEATURE:
<223> OTHER INFORMATION: 2G8 Heavy chain CDR1

<400> SEQUENCE: 4

Gly Tyr Thr Leu Ser Ser Tyr Trp
1               5

<210> SEQ ID NO 5
<211> LENGTH: 24
<212> TYPE: DNA
<213> ORGANISM: Artificial Sequence
<220> FEATURE:
<223> OTHER INFORMATION: 2G8 Heavy chain CDR2

<400> SEQUENCE: 5
attttacctg gaagtggtag tact                                              24

<210> SEQ ID NO 6
<211> LENGTH: 8
<212> TYPE: PRT
<213> ORGANISM: Artificial Sequence
<220> FEATURE:
<223> OTHER INFORMATION: 2G8 Heavy chain CDR2

<400> SEQUENCE: 6

Ile Leu Pro Gly Ser Gly Ser Thr
1               5

<210> SEQ ID NO 7
<211> LENGTH: 27
<212> TYPE: DNA
<213> ORGANISM: Artificial Sequence
<220> FEATURE:
<223> OTHER INFORMATION: 2G8 Heavy chain CDR3

<400> SEQUENCE: 7
gcaagagagg gttggtactt cgatgtc                                           27

<210> SEQ ID NO 8
<211> LENGTH: 9
<212> TYPE: PRT
<213> ORGANISM: Artificial Sequence
<220> FEATURE:
<223> OTHER INFORMATION: 2G8 Heavy chain CDR3

<400> SEQUENCE: 8

Ala Arg Glu Gly Trp Tyr Phe Asp Val
1               5

<210> SEQ ID NO 9
<211> LENGTH: 33
<212> TYPE: DNA
<213> ORGANISM: Artificial Sequence
<220> FEATURE:
<223> OTHER INFORMATION: 2G8 Light chain CDR1

<400> SEQUENCE: 9
cagagcctct tatatagtaa tggaaacacc cat                                    33

<210> SEQ ID NO 10
<211> LENGTH: 11
<212> TYPE: PRT
<213> ORGANISM: Artificial Sequence
<220> FEATURE:
<223> OTHER INFORMATION: 2G8 Light chain CDR1
```

```
<400> SEQUENCE: 10

Gln Ser Leu Leu Tyr Ser Asn Gly Asn Thr His
1               5                   10

<210> SEQ ID NO 11
<211> LENGTH: 9
<212> TYPE: DNA
<213> ORGANISM: Artificial Sequence
<220> FEATURE:
<223> OTHER INFORMATION: 2G8 Light chain CDR2

<400> SEQUENCE: 11 ctggtgtct                                                              9

<210> SEQ ID NO 12
<211> LENGTH: 3
<212> TYPE: PRT
<213> ORGANISM: Artificial Sequence
<220> FEATURE:
<223> OTHER INFORMATION: 2G8 Light chain CDR2

<400> SEQUENCE: 12

Leu Val Ser
1

<210> SEQ ID NO 13
<211> LENGTH: 27
<212> TYPE: DNA
<213> ORGANISM: Artificial Sequence
<220> FEATURE:
<223> OTHER INFORMATION: 2G8 Light chain CDR3

<400> SEQUENCE: 13
gtgcaaggta cactttcc gtacagg                                           27

<210> SEQ ID NO 14
<211> LENGTH: 9
<212> TYPE: PRT
<213> ORGANISM: Artificial Sequence
<220> FEATURE:
<223> OTHER INFORMATION: 2G8 Light chain CDR3

<400> SEQUENCE: 14

Val Gln Gly Thr His Phe Pro Tyr Thr
1               5
```

PROTECTIVE ANTI-GLUCAN ANTIBODIES WITH PREFERENCE FOR β-1,3-GLUCANS

CROSS-REFERENCE TO RELATED APPLICATIONS

This application is a divisional of U.S. application Ser. No. 12/851,962, filed Aug. 6, 2010, now U.S. Pat. No. 8,101,406, which is a continuation of U.S. application Ser. No. 11/662,880, filed Sep. 27, 2007, now U.S. Pat. No. 7,893,219, which is a §371 National Phase filing of PCT/IB2005/003153, filed Sep. 14, 2005, which claims the benefit of GB 0420466.5, filed Sep. 14, 2004, from which applications priority is claimed pursuant to the provisions of 35 U.S.C. §§119/120 and which applications are incorporated by reference herein in their entireties.

All documents cited herein are incorporated by reference in their entirety.

TECHNICAL FIELD

This invention relates to monoclonal antibodies and their use in therapy, particularly in the treatment of fungal infections and disease.

BACKGROUND ART

Fungal infections are prevalent in several clinical settings, particularly in immunocompromised patients. The emergence of resistance to antimycotics, in particular to the azoles, has increased interest in therapeutic and prophylactic vaccination against these fungi [1]. Among fungal pathogens, *Candida albicans* is one of the most prevalent. This organism is one of the principal agents of widespread opportunistic infections in humans and causes candidiasis, a condition which is found in both normal and immunocompromised patients.

There is widespread consensus in the field of medical mycology that cellular immunity is critical for successful host defence against fungi [2], although the potential efficacy of humoral immunity in protecting against two major fungal pathogens (*C. albicans* and *C. neoformans*) has attracted attention [3]. For *C. neoformans*, antibodies to the capsular glucuronoxylomannan have been shown to mediate protection in animal models of infection. For *C. albicans*, cell-surface mannoproteins are the dominant antigenic components of *C. albicans* and antibodies to mannan, proteases and a heat shock proteins have been associated with protection against infection. Other vaccine candidates include: members of the aspartyl proteinase (Sap2) family; the 65 kDa mannoprotein (MP65) [4]; adhesion molecules isolated from phosphomannan cell wall complexes [5]; peptides which mimic epitopes from the mannan portion of the phosphomannan complex of *Candida* [6]; and hemolysin-like proteins [7].

Glucans are glucose-containing polysaccharides found inter alia in fungal cell walls. α-glucans include one or more α-linkages between glucose subunits and β-glucans include one or more β-linkages between glucose subunits. Within a typical fungal cell wall, β-1,3-glucan microfibrils are interwoven and crosslinked with chitin microfibrils to form the inner skeletal layer, whereas the outer layer consists of β-1,6-glucan and mannoproteins, linked to the inner layer via chitin and β-1,3-glucan.

In *C. albicans*, 50-70% of the cell wall is composed of β-1,3- and β-1,6-glucans. Protective antibodies against *C. albicans* β-1,6-glucan have been generated in mice [8]. Mice in which anti β-1,6-glucan antibodies were raised by idiotypic vaccination with mannoprotein-depleted *C. albicans* cells were shown to have some protection against systemic challenge by *C. albicans*. Furthermore, mice passively immunised with these anti β-1,6-glucan antibodies demonstrated a raised level of protection against *C. albicans*.

It is an object of the invention to provide further and better monoclonal antibodies for inducing therapeutic immune responses against infections, particularly against microbial infections.

DISCLOSURE OF THE INVENTION

β-1,3-glucans are a cell wall component of many microbes but are naturally poor immunogens. As such, anti-β-1,3-glucan antibodies have not previously been specifically considered for use in therapy. As discussed above, anti-β-1,6-glucan antibodies are known to provide some protection against fungal challenge. The present inventors have discovered that anti-β-1,3-glucan antibodies can be more effective against fungal challenge than anti-β-1,6-glucan antibodies.

The present invention thus relates to monoclonal antibodies that detect and bind to β-1,3-glucan, hybridoma cell lines producing the antibodies, and methods of using such antibodies for treatment of microbial infections, particularly against *Candida albicans* or *Aspergillus fumigatis* infection. The antibodies of the present invention are not specific for β-1,6-glucan.

Antibodies of the Invention

The invention provides monoclonal antibodies that can protect a mammal against infection by a microbial pathogen, wherein the pathogen has a cell wall containing β-1,3-glucan and β-1,6-glucan, and wherein the monoclonal antibody shows preferential binding to the β-1,3-glucan over the β-1,6-glucan. The antibodies preferably have microbicidal activity. The invention also provides fragments of these monoclonal antibodies, particularly fragments that retain the antigen-binding activity of the antibodies.

An antibody shows preferential binding to a β-1,3-glucan over a β-1,6-glucan if, under the same conditions, it binds more strongly (as measured, for instance, as optical density (OD) readings in an indirect ELISA test) with a β-1,3-glucan than with a β-1,6-glucan. Differential reactivity can be determined, for example, by incubating a constant antibody concentration with scalar concentrations of antigen (β-1,3-glucan and β-1,6-glucan). A higher concentration (e.g. $\geq 10\times$, $>100\times$) of the lower affinity antigen will be required to give equivalent OD readings.

Alternatively, competitive-inhibition ELISA experiments can be used to determine differential binding. For example, each antibody is reacted with cell wall glycans and either β-1,3-glucan or β-1,6-glucan is added as a soluble-phase competitor. An antibody shows preferential binding to a β-1,3-glucan over a β-1,6-glucan if, for example, the concentration of free β-1,3-glucan required to cause 50% inhibition of antibody binding to cell wall glycans is $>10\times$ lower than the concentration of free β-1,6-glucan required to cause 50% inhibition of antibody binding to the same cell wall glycans. For *C. albicans*, the cell wall glycans are preferably 'GG-zym' soluble glucan antigens [8]. These are obtained by (i) preparing glucan ghosts by repeated hot alkali-acid extractions of fungal cell walls to give purified β-1,3- and β-1,6-glucans and (ii) digesting the ghosts with β-1,3-glucanase for 1 hour at 37° C. The glycans may be immobilised for inhibition testing.

The term 'monoclonal antibody' includes any of the various artificial antibodies and antibody-derived proteins which are available e.g. human antibodies, chimeric antibodies, humanized antibodies, single-domain antibodies, single-chain Fv (scFV) antibodies, monoclonal oligobodies, dimeric or trimeric antibody fragments or constructs, minibodies, or functional fragments thereof which bind to the antigen in question.

In a natural antibody molecule, there are two heavy chains and two light chains. Each heavy chain and each light chain has at its N-terminal end a variable domain. Each variable domain is composed of four framework regions (FRs) alternating with three complementarity determining regions (CDRs). The residues in the variable domains are conventionally numbered according to a system devised by Kabat et al. [9]. The Kabat residue designations do not always correspond directly with the linear numbering of the amino acid residues and the linear amino acid sequence may contain fewer or additional amino acids than in the strict Kabat numbering. This may correspond to a shortening of, or insertion into, a structural component, whether framework or CDR, of the basic variable domain structure.

A preferred antibody of the invention is 2G8 (SEQ ID NOs: 1 and 2). The heavy chain variable domain of 2G8 (SEQ ID NO: 2) comprises CDRs which are located at residues 23-30 (CDR-H1, SEQ ID NO: 4), residues 48-55 (CDR-H2, SEQ ID NO: 6) and residues 94-102 (CDR-H3, SEQ ID NO: 8). The light chain variable domain of 2G8 (SEQ ID NO: 1) comprises CDRs which are located at residues 27-37 (CDR-L1, SEQ ID NO: 10), residues 55-58 (CDR-L2, SEQ ID NO: 12) and residues 94-102 (CDR-L3, SEQ ID NO: 14).

Antibodies having specificity for β-glucan and comprising one or more (e.g. 1, 2, 3, 4, 5 or 6) of the CDRs from 2G8 are also preferred, as are derivatives of 2G8 in which one or more (e.g. 2, 3, 4, 5, 6, 7, 8, 9, 10, 11, 12, 13, 14, 15) framework residues are substituted with other amino acids. Fusion proteins comprising 2G8 or derivatives, at the N- of C-terminus are also useful. The 2G8 CDRs may optionally each contain 1, 2, 3 or 4 amino acid substitutions.

Preferably, the heavy chain of the antibodies of the invention comprises one or more (e.g. 1, 2, or 3) of the CDRs encoded by SEQ ID NOs 3, 5 and 7. Preferably, the light chain of the antibodies of the invention comprises one or more (e.g. 1, 2, or 3) of the CDRs encoded by SEQ ID NOs 9, 11 and 13.

Antibody 2G8 is derived from a mouse. To avoid a non-specific anti-mouse immune response in humans, the antibodies of the invention are preferably humanized or chimeric. [e.g. refs. 10 & 11]. As an alternative, fully-human antibodies may be used.

In chimeric antibodies, non-human constant regions are substituted by human constant regions but variable regions remain non-human. Humanized antibodies may be achieved by a variety of methods including, for example: (1) grafting complementarity determining regions (CDRs) from the non-human variable region onto a human framework ("CDR-grafting"), with the optional additional transfer of one or more framework residues from the non-human antibody ("humanizing"); (2) transplanting entire non-human variable domains, but "cloaking" them with a human-like surface by replacement of surface residues ("veneering"). In the present invention, humanized antibodies include those obtained by CDR-grafting, humanizing, and veneering of the variable regions. [e.g. refs. 12 to 18].

Humanized or fully-human antibodies can also be produced using transgenic animals that are engineered to contain human immunoglobulin loci. For example, ref. 19 discloses transgenic animals having a human Ig locus wherein the animals do not produce functional endogenous immunoglobulins due to the inactivation of endogenous heavy and light chain loci. Ref. 20 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. Ref. 21 discloses the use of the Cre/Lox system to modify the immunoglobulin locus in a mammal, such as to replace all or a portion of the constant or variable region to form a modified antibody molecule. Ref. 22 discloses non-human mammalian hosts having inactivated endogenous Ig loci and functional human Ig loci. Ref 23 discloses methods of making transgenic mice in which the mice lack endogenous heavy chains, and express an exogenous immunoglobulin locus comprising one or more xenogeneic constant regions.

Antibodies naturally have two separate chains, however, it is preferred to use a single chain antibody ("sFv") in which the light and heavy chain variable domains are joined by a linker to give a single polypeptide chain. Kits for preparing scFv's are available off-the-shelf, and anti-ligand scFvs are preferred second sequences for use with the invention. Single domain antibodies can also be obtained from camelids or sharks [24], or by camelisation [25].

A sFv polypeptide is a covalently linked $V_H$-$V_L$ heterodimer which is expressed from a gene fusion including $V_H$- and $V_L$-encoding genes linked by a peptide-encoding linker [26]. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., references 27 to 29. The sFv molecules may be produced using methods described in the art. Design criteria include determining the appropriate length to span the distance between the C-terminus of one chain and the N-terminus of the other, wherein the linker is generally formed from small hydrophilic amino acid residues that do not coil or form secondary structures. Such methods have been described in the art [e.g. refs. 27-29]. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains which include oligomerization domains at their C-termini, separated from the sFv by a hinge region [30]. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g references 30 & 31.

"Oligobodies" will also find use with the present invention. Oligobodies are synthetic antibodies. The specificity of these reagents has been demonstrated by Western blot analysis and immunohistochemistry. They have some desirable properties, namely that as their production is independent of the immune system, they can be prepared in a few days and there is no need for a purified target protein [32]. Oligobodies are produced using recombinant methods well known in the art [33].

Antibodies of the invention are preferably neutralising antibodies i.e. they can neutralise the ability of a pathogen (e.g. of *C. albicans*) to initiate and/or perpetuate an infection in a host. The antibody can preferably neutralise at a concentration of $10^{-9}$M or lower (e.g. $10^{-10}$M, $10^{-11}$M, $10^{-12}$M or lower).

Antibodies are produced using techniques well known to those of skill in the art [e.g. refs. 34-39]. Monoclonal antibodies are generally prepared using the method of Kohler & Milstein (1975) [40], or a modification thereof. Typically, a mouse or rat is immunized as described above. Rabbits may also be used. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine aminopterin thymidine medium, 'HAT'). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

The invention also provides a hybridoma expressing the antibody of the invention. This hybridoma can be used in various ways e.g. as a source of monoclonal antibodies or as a source of nucleic acid (DNA or mRNA) encoding the monoclonal antibody of the invention for the cloning of antibody genes for subsequent recombinant expression.

Antibodies of the invention may be produced by any suitable means (e.g. by recombinant expression). Expression from recombinant sources is more common for pharmaceutical purposes than expression from B cells or hybridomas e.g. for reasons of stability, reproducibility, culture ease, etc.

The invention provides a method for preparing one or more nucleic acid molecules (e.g. heavy and light chain genes) that encodes an antibody of interest, comprising the steps of: (i) preparing a hybridoma expressing the antibody of the invention as described above; (ii) obtaining from the hybridoma nucleic acid that encodes the antibody of interest. The invention also provides a method for obtaining a nucleic acid sequence that encodes an antibody of interest, comprising the steps of: (i) preparing a hybridoma according to the invention; (ii) sequencing nucleic acid from the hybridoma that encodes the antibody of the present invention.

Thus the invention also provides a method for preparing a recombinant cell, comprising the steps of: (i) preparing a hybridoma expressing the antibody of the invention as described above; (ii) obtaining one or more nucleic acids (e.g. heavy and/or light chain genes) from the hybridoma; (iii) inserting the nucleic acid into an expression vector; and (iv) transforming an expression host with the expression vector in order to permit expression of the antibody of interest in that host.

Similarly, the invention also provides a method for preparing a recombinant cell, comprising the steps of: (i) preparing a hybridoma expressing the antibody of the invention as described above; (ii) sequencing nucleic acid(s) from the hybridoma that encodes the antibody of interest; (iii) using the sequence information from step (ii) to prepare nucleic acid(s) for inserting into an expression vector; and (iv) transforming an expression host with the expression vector in order to permit expression of the antibody of interest in that host.

A single expression vector may be constructed which contains the nucleic acid sequences coding for more than one of the antibody chains. For instance, the nucleic acid sequences encoding the heavy and light chains may be inserted at different positions on the same expression vector. Alternatively, the nucleic sequence coding for each chain, may be inserted individually into an expression vector, thus producing a number of constructed expression vectors, each coding for a particular chain. Preferably, the expression vectors into which the sequences are inserted are compatible.

The transformed cells of the invention can then be used for expression and culture purposes. They are particularly useful for expression of antibodies for large-scale pharmaceutical production. They can also be used as the active ingredient of a pharmaceutical composition. Any suitable culture techniques can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from hybridomas are well known in the art e.g. see chapter 4 of ref. 41.

The expression host is preferably a eukaryotic cell, including yeast and animal cells, particularly mammalian cells (e.g. CHO cells, human cells such as PER.C6 (Crucell [42]) or HKB-11 (Bayer; [43,44]) cells, myeloma cells [45,46], etc.), as well as plant cells. Preferred expression hosts can glycosylate the antibody of the invention, particularly with carbohydrate structures that are not themselves immunogenic in humans. Expression hosts that can grow in serum-free media are preferred. Expression hosts that can grow in culture without the presence of animal-derived products are preferred.

The expression host may be cultured to give a cell line.

Antibody fragments which retain the ability to recognise a β-1,3-glucan antigen are also included within the scope of the invention. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')$_2$ fragments. These fragments will contain two antigen binding sites, but lack a portion of the constant region from each of the heavy chains. Similarly, if desired, Fab fragments, comprising a single antigen binding site, can be produced, e.g., by digestion of monoclonal antibodies with papain. Functional fragments, including only the variable regions of the heavy and light chains, can also be produced, using standard techniques such as recombinant production or preferential proteolytic cleavage of immunoglobulin molecules. These fragments are known as Fv. See, e.g., references 47 to 49.

Non-conventional means can also be used to generate and identify the antibodies of the invention. For example, a phage display library can be screened for antibodies of the invention [50-53].

Monoclonal antibodies are particularly useful in identification and purification of the individual polypeptides or other antigens against which they are directed. The monoclonal antibodies of the invention have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme. For example, the monoclonal antibodies of the invention may be used to detect circulating β-1-3 glucan in patients suffering from candidiasis or aspergillosis [54].

Antibodies of the invention can be coupled to a drug for delivery to a treatment site or coupled to a detectable label to facilitate imaging of a site comprising cells of interest, such as cancer cells. Methods for coupling antibodies to drugs and detectable labels are well known in the art, as are methods for imaging using detectable labels.

Antibodies of the invention may be attached to a solid support.

Antibodies of the invention can be of isotype IgA or, preferably, IgG, i.e. an α or γ heavy chain. Within the IgG isotype, antibodies may be IgG1, IgG2, IgG3 or IgG4 subclass. Antibodies of the invention may have a κ or a λ light chain.

Microbicidal Activity

The monoclonal antibody of the invention preferably has microbicidal activity.

Preferably, it has anti-mycotic activity and/or anti-bacterial activity. Anti-bacterial activity may be against a Gram-negative or Gram-positive bacterium.

More preferably, it has activity against a microbe which has a glucan-based cell wall.

More preferably, it has activity against a microbe which comprises a β-1,3-linked oligosaccharide cell wall.

Most preferably, it has activity against *Candida albicans* and/or against *Aspergillus fumigates*.

Pharmaceutical Compositions

The use of monoclonal antibodies as the active ingredient of pharmaceuticals is now widespread, including the products Herceptin™ (trastuzumab), Rituxan™, Campath™, Remicade™, ReoPro™, Mylotarg™, Zevalin™, Omalizumab, Synagis™ (Palivizumab), Zenapax™ (daclizumab), etc. These include antibodies that recognise human self-antigens (e.g. Herceptin™ recognises the Her2 marker) and antibodies that recognise antigens from pathogens (e.g. Synagis™ recognises an antigen from respiratory syncytial virus).

The invention provides a pharmaceutical composition comprising (1) monoclonal antibody of the invention and (2) a pharmaceutically acceptable carrier.

The invention provides a method of preparing a pharmaceutical, comprising the steps of: (i) preparing a monoclonal antibody of the invention; and (ii) admixing the purified antibody with one or more pharmaceutically-acceptable carriers.

The composition is preferably substantially free from antibodies which inhibit the protective efficacy of the anti-glucan antibodies. For example, where the glucan is a fungal β-1,3-glucan then the composition is preferably substantially free from antibodies against non-glucan cell wall components, such as anti-mannoprotein antibodies.

Component (1) is the active ingredient in the composition, and this is present at a therapeutically effective amount i.e. an amount sufficient to inhibit microbial/viral growth and/or survival in a patient, and preferably an amount sufficient to eliminate microbial infection. The precise effective amount for a given patient will depend upon their size and health, the nature and extent of infection, and the composition or combination of compositions selected for administration. The effective amount can be determined by routine experimentation and is within the judgement of the clinician. For purposes of the present invention, an effective dose will generally be from about 0.01 mg/kg to about 5 mg/kg, or about 0.01 mg/kg to about 50 mg/kg or about 0.05 mg/kg to about 10 mg/kg of the compositions of the present invention in the individual to which it is administered. Known antibody pharmaceuticals provide guidance in this respect e.g. Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc. Pharmaceutical compositions based on polypeptides, antibodies and nucleic acids are well known in the art. Polypeptides may be included in the composition in the form of salts and/or esters.

Carrier (2) can be any substance that does not itself induce the production of antibodies harmful to the patient receiving the composition, and which can be administered without undue toxicity. Suitable carriers can be large, slowly metabolised macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers can include liquids such as water, saline, glycerol and ethanol. Auxiliary substances, such as wetting or emulsifying agents, pH buffering substances, and the like, can also be present in such vehicles. Liposomes are suitable carriers. A thorough discussion of pharmaceutical carriers is available in ref. 55.

Pharmaceutical compositions of the invention may also be used prophylactically e.g. in a situation where contact with microbes is expected and where establishment of infection is to be prevented. For instance, the composition may be administered prior to surgery.

In compositions of the invention that include antibodies of the invention, the antibodies preferably make up at least 50% by weight (e.g. 60%, 70%, 80%, 90%, 95%, 97%, 98%, 99% or more) of the total protein in the composition. The antibodies are thus in purified form.

Microbial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition, like Synagis™ and Herceptin™, for reconstitution with sterile water containing a preservative). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 56]. The composition may be included in a mouthwash. The composition may be lyophilised.

The pharmaceutical composition is preferably sterile. It is preferably pyrogen-free. It is preferably buffered e.g. at between pH 6 and pH 8, generally around pH 7. Preferably, the composition is substantially isotonic with humans.

The invention also provides a delivery device containing a pharmaceutical composition of the invention. The device may be, for example, a syringe or an inhaler.

Compositions of the invention may be used in conjunction with known anti-fungals. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also ref. 57]. Compositions may also be used in conjunction with known anti-virals e.g. HIV protease inhibitors, a 2',3'-dideoxynucleoside (e.g. DDC, DDI), 3'-azido-2',3'-dideoxynucleosides (AZT), 3'-fluoro-2',3'-dideoxynucleosides (FLT), 2',3'-didehydro-2',3'-dideoxynucleosides (e.g. D4C, D4T) and carbocyclic derivatives thereof (e.g. carbovir), 2'-fluoro-ara-2',3'-dideoxynucleosides, 1,3-dioxolane derivatives (e.g. 2',3'-dideoxyl-3'-thiacytidine), oxetanocin analogues and carbocyclic derivatives thereof (e.g. cyclobut-G) and the 9-(2- phosphonylmethoxyethyl)adenine (PMEA) and 9-(3-fluoro-2-phosphonylmethoxypropyl)adenine (FPMPA) derivatives, tetrahydro-imidazo[4,5,1-jk][1,4]-benzodiazepin-2(1H)one (TIBO), 1-[(2-hydroxyethoxy)-methyl]-6-(phenylthio) thymine (HEPT), dipyrido[3,2-b:2',3'-e]-[1,4]diazepin-6-one (nevirapine) and pyridin-2(1H)one derivatives, 3TC, etc.

Medical Treatments and Uses

The antibody is a protective, offering protection against microbial infection and/or disease.

Thus, the invention provides a monoclonal antibody of the invention for use as a medicament. The invention also provides a method for protecting a patient from a microbial infection, comprising administering to the patient a pharmaceutical composition of the invention. The invention also provides the use of monoclonal antibody of the invention in the manufacture of a medicament for the prevention of microbial infection and/or disease.

As well as being used in preventative methods, the antibody can also be used to treat an existing microbial infection and/or disease.

Thus, the invention also provides a method for treating a patient suffering from a microbial infection, comprising administering to the patient a pharmaceutical composition of the invention. The invention also provides the use of monoclonal antibody of the invention in the manufacture of a medicament for treating a patient.

The microbe may be a fungus or a bacterium, examples of which are given below.

The patient is preferably a human, particularly a female. The human may be an adult or a child.

The antibodies of the invention are particularly useful for treating microbial infections in patients who are: pregnant; immunocompromised/immunosuppressed (T-cell deficient); or undergoing antibiotic therapy or chemotherapy. The antibodies of the invention are also useful for treating microbial infection in patients who have: systemic microbial infection; indwelling intravascular catheters; HIV; AIDS; neutropenia; previous fungal colonisation; diabetes; leukaemia; lymphoma; burns; maceration; oral cavity infections and patients who have had prior hemodialysis or who have undergone organ transplants.

These uses and methods are particularly useful for treating infections of: *Candida* species, such as *C. albicans*; *Cryptococcus* species, such as *C. neoformans*; *Enterococcus* species, such as *E. faecalis*; *Streptococcus* species, such as *S. pneumoniae, S. mutans, S. agalactiae* and *S. pyogenes*; *Leishmania* species, such as *L. major* and *L. infantum*; *Acanthamoeba* species, such as *A. castellani*; *Aspergillus* species, such as *A. fumigatus* and *A. flavus*; *Pneumocystis* species, such as *P. carinii*; *Mycobacterium* species, such as *M. tuberculosis*; *Pseudomonas* species, such as *P. aeruginosa*; *Staphylococcus* species, such as *S. aureus*; *Salmonella* species, such as *S. typhimurium*; *Coccidioides* species such as *C. immitis*; *Trichophyton* species such as *T. verrucosum*; *Blastomyces* species such as *B. dermatidis*; *Histoplasma* species such as *H. capsulatum*; *Paracoccidioides* species such as *P. brasiliensis*; *Pythiumn* species such as *P. insidiosum*; and *Escherichia* species, such as *E. coli*.

The uses and methods are particularly useful for treating diseases including, but not limited to: candidosis, aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, keratitis, cystic fibrosis, typhoid fever, gastroenteritis and hemolytic-uremic syndrome. Anti-*C. albicans* activity is particularly useful for treating infections in AIDS patients.

Efficacy of treatment can be tested by monitoring microbial infection after administration of the pharmaceutical composition of the invention.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal patch, ocular, nasal, aural, or pulmonary administration. Injection or intranasal administration is preferred. It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

Dosage treatment can be a single dose schedule or a multiple dose schedule.

As an alternative to delivering monoclonal antibodies for therapeutic purposes, it is possible to deliver nucleic acid (typically DNA) to a subject that encodes the monoclonal antibody (or active fragment thereof) of interest, such that the nucleic acid can be expressed in the subject in situ to provide a desired therapeutic effect. Suitable gene therapy and nucleic acid delivery vectors are known in the art General The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Where the invention refers to antibodies that have two chains (heavy and light), the invention also encompasses where appropriate the individual chains separately from each other.

MODES FOR CARRYING OUT THE INVENTION

Figure 1:
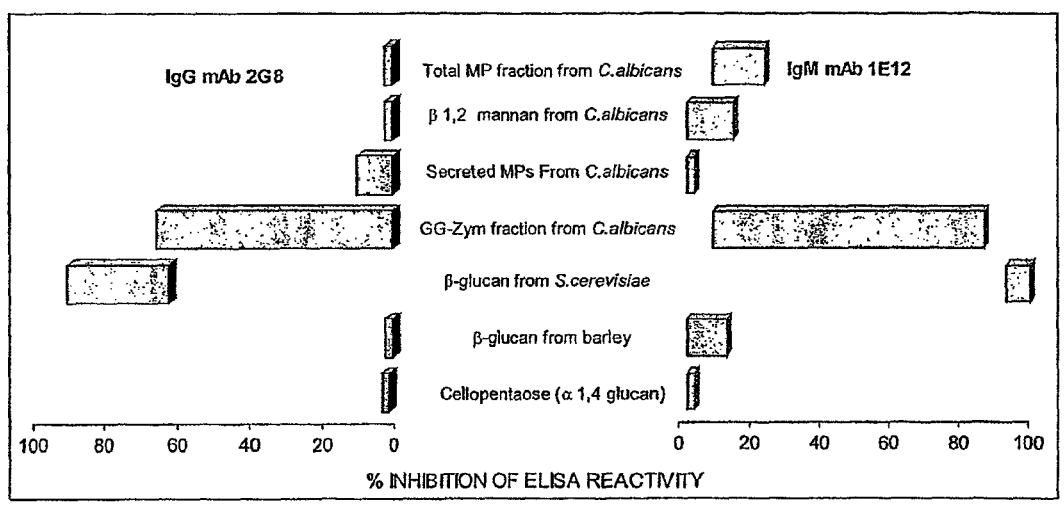
FIG. 1 shows the results of an inhibition ELISA test using putative competitor ligands against IgG 2G8 and IgM 1E12 mAbs. Percent inhibition values are shown for each putative inhibitor at the four doses tested, and the graph refers to one representative experiment of two with similar results.

I. Hybridoma Generation and Monoclonal Antibody Purification

Two female Balb/c mice (Harlan) were immunized with 15 μg polysaccharide/mouse (corresponding to 25μ protein/mouse) of a glycoconjugate between purified β-glucan preparation from the cell wall of *C. albicans* and the diphtheria genetic toxoid CRM197 (GG-Zym Pool 1-CRM 197 conjugate; [8]).

The conjugate was administered once subcutaneously, in complete Freund's adjuvant, and twice intraperitoneally, at weekly intervals, without, adjuvant. The final boosting dose (5 μg polysaccharide/mouse) was given intravenously 4 days before the fusion.

Spleen cells of immunized mice were fused at a 1:1 ratio with myeloma cells of the murine line X63-Ag8 653 by standard techniques and hybrids were selected according to standard protocols (see also [58]). Culture supernatants were screened for antibody production by an indirect ELISA [59], using the *C. albicans* glucan purified extract GG-Zym or standard glucan compounds (laminarin, pustulan) as coating antigens and an alkaline phosphatase-conjugate goat, polyvalent anti-mouse immunoglobulins antibody (Sigma) as the secondary antibody.

Anti-glucan antibody-secreting hybridoma cultures were cloned twice by limiting dilution and subsequently grown in vitro in RPMI 1640 (Hyclone) supplemented with 10% fetal calf serum (Hyclone), 100 U penicillin/ml, 100 μg streptomycin/ml, 1 mM sodium pyruvate and 2 mM L-glutamine (Hyclone).

A number of stable hybridoma were obtained through this procedure. Monoclonal antibodies (mAb) produced by them could be purified from culture supernatants by ammonium sulphate precipitation followed by centrifugation and extensive dialysis of the precipitate against PBS. Purity of precipitated mAbs was evaluated by SDS-PAGE followed by Coomassie blue staining. Titers of mAb preparations were determined by indirect ELISA against the different glucan antigens and defined as the highest dilution of the antibody giving at least twice the absorbance values obtained for the negative control (buffer only).

2. Determination of the Immunoglobulin Class and Isotype

One hybridoma of interest was designated '2G8'. It was attributed to the IgG class according to its SDS-PAGE profile and reactivity in ELISA and western blot assays with affinity isolated, alkaline phosphatase-conjugated goat anti-mouse γ chain antibodies (Sigma). ELISA reactivity with affinity purified, biotin-conjugated anti-mouse IgG1, IgG2a, IgG2b or IgG3 monoclonal antibodies (BD-Pharmingen) indicated that the IgG mAb 2G8 belonged to the IgG2b isotype. A second antibody (1E12) was similarly attributed to the IgM class. 1E12 served as a control in later experiments.

3. Sequencing of the Monoclonal Antibody Variable Regions

The sequences of the VL and VH regions of 2G8 antibody and of the control IgM antibody were determined. Each V region contains three CDRs indicated as CDR1, CDR2 and CDR3 in one framework region. mRNA was extracted from the hybridoma cells expressing 2G8 and control IgM and the corresponding cDNA was synthesised through amplification GAP-DH gene. The VL and VH genes were amplified and products were extracted by agarose gel electrophoresis. The VH and VL regions were then cloned into the plasmid vector pCR-BluntII-TOPO. The bacterial strain Top 10 was transformed with the plasmid vector and transformants were analysed. DNA was then extracted and sequenced.

The sequences of the heavy and light chain variable regions of 2G8 are given as SEQ IN NO:1 and SEQ ID NO:2. The CDRs within these sequences are given as SEQ ID NO:3, SEQ ID NO:5, SEQ ID NO:7, SEQ ID NO:9, SEQ ID NO:11 and SEQ ID NO:13. The same variable region sequences were found in the IE12 IgM.

4. Specificity of IgG mAb 2G8 and IgM Control mAb

To investigate the nature of the epitopes preferred by mAbs, we devised an inhibition ELISA test employing the unfractionated GG-Zym antigen as the solid-phase reagent, and distinct glucan or non-glucan cell wall fractions from *C. albicans*, or standard glucan compounds, as free-phase mAb ligands in a competition reaction with the GG-Zym antigen. This approach was chosen because of the possible inability of some of the putative mAb ligands to adsorb effectively to the plastic.

Putative inhibitors, at the concentration of 50, 10, 5 and 1 μg/ml were added to appropriate mAb dilutions in PBS, and incubated o.n. at room temperature. The reacted mixtures were then added to duplicate wells coated with GG-Zym (50 μg/ml in carbonate buffer). ELISA tests were then performed as previously reported [60], using phosphatase-conjugated anti-mouse IgG and anti-mouse IgM antibody (Sigma) as the secondary reagents for mAb 2G8 and IgM control antibodies, respectively. Percent inhibition by the various free-phase mAb ligands was calculated by comparing O.D.405 nm from wells containing the putative inhibitors with the O.D.405 nm from wells without inhibitors (ranging usually from 0.8 to 0.65 in the different experiments). Readings from negative control wells (buffer only) were subtracted from all O.D. values.

As shown in FIG. 1, the use of non-glucan fungal fraction as competitor ligands, such as a total mannoprotein (MP) extract from C. albicans, or a preparation of MPs secreted by the fungus, or even a particular cell wall mannan moiety with similar β conformation as glucan (β1,2 mannan), only produced a non significant or a very weak inhibition of ligation of 2G8 or IgM control mAbs with the GG-Zym fraction. This also occurred when cellopentaose, a non-β-glucan compound, was used as the competitor ligand. This indicates that neither a β conformation, nor the mere presence of a sequence of glucose residues were per se sufficient for mAb recognition and ligation.

Conversely, a substantial inhibition of the reactivity of both mAbs was observed when the GG-Zym fraction (0-65 and 10-87 percent inhibition for mAb 2G8 and IgM control mAb, respectively, when used at the concentration of 1 or 50 µg/ml) was used as an inhibitor, and a nearly complete inhibition by a commercial β-glucan preparation from the yeast *Saccharomyces cerevisiae* (64-90 and 91-100 percent inhibition for mAb 2G8 and IgM control mAb, respectively when used at 1 or 50 µg/ml). A commercial, non-fungal preparation of β-glucan (barley β-glucan) was almost totally ineffective as competitor ligand for both mAbs.

Overall, these results indicated that mAb 2G8 and the IgM control mAb recognised epitopes that are specifically contained in β-glucan extracts. The total MP fraction from *C. albicans*, which exert a weak inhibitory effect on mAb reactivity, has been reported to contain a small amount of β-glucan [61]. In addition, mAb specificity is not restricted to β-glucan from *C. albicans*, the source of the immunising antigen, but to be extended to glucans from other yeast species, according to the known structural homogeneity of fungal glucans. This has implications for the control of many other fungal pathogens that express critical β-glucan molecules in their cell wall (see below).

5. Chemical Nature of the Epitopes Recognised by 2G8 and IgM Control mAb

The same ELISA inhibition test described above was used to define more precisely the chemical nature of mAb epitopes, by the use of chemically defined standard β-1,3 and β-1,6 glucans. In particular, laminarin (Sigma), a well characterised preparation from *Laminaria digitata*, which is mostly composed by β-1,3-linked glucose residues with few, short β-1,6-linked side chains, and a series of linear β-1,3-linked, laminarioligosaccharides with different degree of polymerisation (two to seven) were used. Pustulan (CalbioChem), a standard linear β-1,6-linked glucan from *Umbilicaria papullosa* and gentiobiose (β-D-Glc-(1,6)-D-Glc) was also assayed. Two subfractions separated by gel filtration from the GG-Zym antigen, GG-Zym Pool 1 and GG-Zym Pool 2, were also included in the experiments.

Appropriate mAb dilutions were reacted overnight with inhibitors at 50, 10 or 5 µg/ml and then added to duplicate wells coated with GG-Zym. ELISA tests were then carried out, using phosphatase-conjugated anti-mouse IgG and anti-mouse IgM antibody (Sigma) as the secondary reagents for mAb 2G8 and IgM control mAb, respectively. Percent inhibition by the various free-phase mAb ligands was calculated as before.

Figure 2:
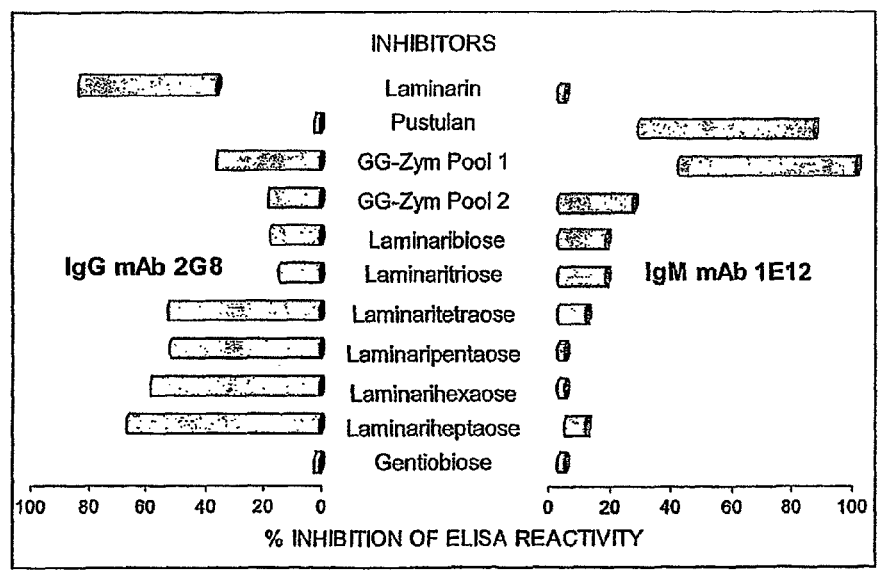
FIG. 2 shows the results of an inhibition ELISA test using chemically defined β-1,3 and β-1,6 standards. Values in the graph are ranges of percent inhibition measured for each inhibitor at the three doses tested, and refer to a representative experiment out of two performed with similar results.

Results from a typical ELISA inhibition test performed with these materials are shown in FIG. 2.

In these experiments, the two mAbs demonstrated a distinctive binding preferences towards laminarin and pustulan. In fact, reactivity of mAb 2G8 was almost totally abolished by preincubation with laminarin (38 and 89 percent inhibition by 5 and 50 µg/ml, respectively) but not at all by pustulan. On the contrary, pustulan, but not laminarin, was a preferential ligand for the IgM control mAb (24 and 90 percent inhibition at 5 and 50 µg/ml, respectively).

Therefore, it was concluded that mAb 2G8 had a binding preference for glucan in β-1,3 configuration. whereas the control IgM mAb demonstrated a binding preference for glucan in β-1,6 conformation. Preferential binding of mAb 2G8 to β-1,3 glucan was confirmed by the observation that chemically defined β-1,3-linked oligosaccharides (DP of 4 to 7) could also efficiently compete for mAb 2G8 ligation, whereas they are not recognised by the IgM mAbcontrol. However, it was also observed that oligosaccharides of β-1,3 conformation with lower DP (2 or 3), but not the β-1,6-linked gentiobiose, could exert a mAb-unspecific, weak inhibitory effect. This suggested that small molecules in β-1,3 conformation may be recognised by both mAbs though with a low affinity and specificity.

This latter observation could also contribute to explain the fact that the GG-Zym sub-fraction Pool 2 weakly affected reactivity of both mAbs, as this sub-fraction is a mixture of small β-1,3 oligosaccharides with a predominant DP 3 [62]. In contrast, the Pool 1 sub-fraction showed a definitely higher affinity for the IgM control mAb, in good accordance with its structure predominantly constituted by β-1,6-linked chains.

Figure 3:
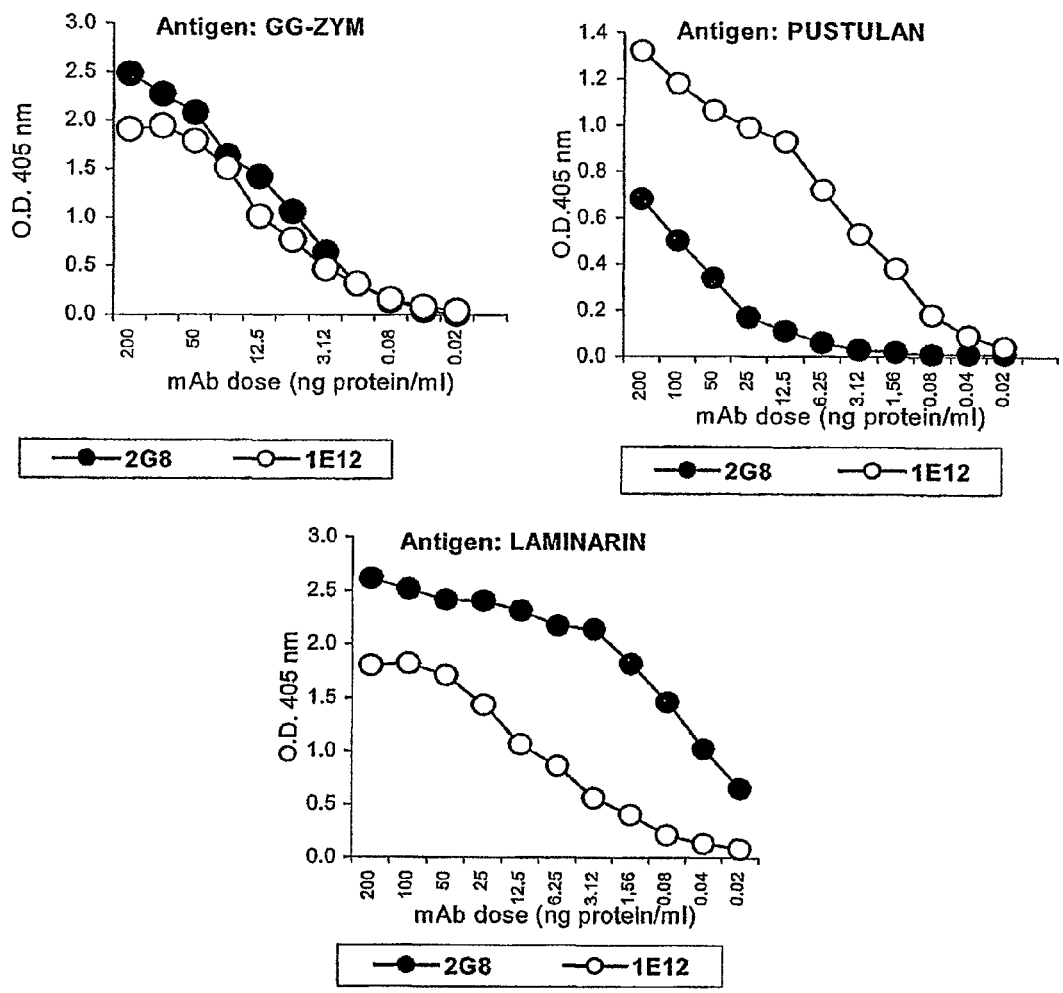
FIG. 3 shows the results of experiments to determine the binding of IgG mAb 2G8 and IgM control mAb to distinct, plastic-adsorbed glucan antigens.

6. Binding of IgG mAb 2G8 and IgM Control mAb to Distinct, Plastic-Adsorbed Glucan Antigens ELISA plates coated with GG-Zym, pustulan or laminarin were reacted with decreasing amounts of 2G8 or control mAb (purified, ammonium sulphate-precipitated preparations from culture supernatants in synthetic, protein-free medium) and developed with specific, anti mouse IgM or IgG, AP-conjugated secondary antibodies followed by the enzyme substrate. FIG. 3 shows O.D. 405 nm absorbance readings generated by the mAbs reacting with distinct glucan antigens, as indicated.

As shown in FIG. 3, the 2G8 and the control mAbs exhibited different affinities towards glucan molecules of different molecular conformation. In particular, the IgM control mAb preferentailly binds β(1-6) glucan, compared to the IgG mAb 2G8. Approximately 3.0 ng/ml of IgM control mAb generated an O.D.405 nm value of 0.5, upon reaction with pustulan, whereas at least 100 ng/ml of the IgG 2G8 mAb were required to obtain the same O.D. reading. Furthermore, the IgG 2G8 mAb preferentially binds the β(1-3) glucan, since only 0.04 ng/ml were able to produce an O.D. of 1.0 by reacting with laminarin, when compared to approximately 10 ng/ml of IgM mAb required to obtain the same level of biding to this antigen. As a control, the two mAbs were also tested for binding to GG-Zym, a β(1-6) and β(1-3) glucan-containing preparation from *C. albicans* and, as expected, the mAbs showed an overlapping binding curve upon reaction with this composite glucan fraction containing both conformations.

7. Inhibition of mAb Binding to GG-Zym by β-Glucan Compounds with Distinct Molecular Structures We further investigated the affinity of the two mAbs for glucan molecules of different conformation by performing ELISA inhibition experiments. Fixed concentrations of mAbs were reacted with plastic-immobilized GG-Zym in the presence of increasing concentrations of laminarin, pustulan or β-glucan from *S. cerevisiae*. Ability of these free-phase ligands to compete with GG-Zym for mAb binding was evaluated by comparing the O.D.405 nm readings obtained in the precence of the inhibitors with those measured in the absence of inhibitors. Results were expressed as percent inhibition of ELISA reactivity.

Figure 4:
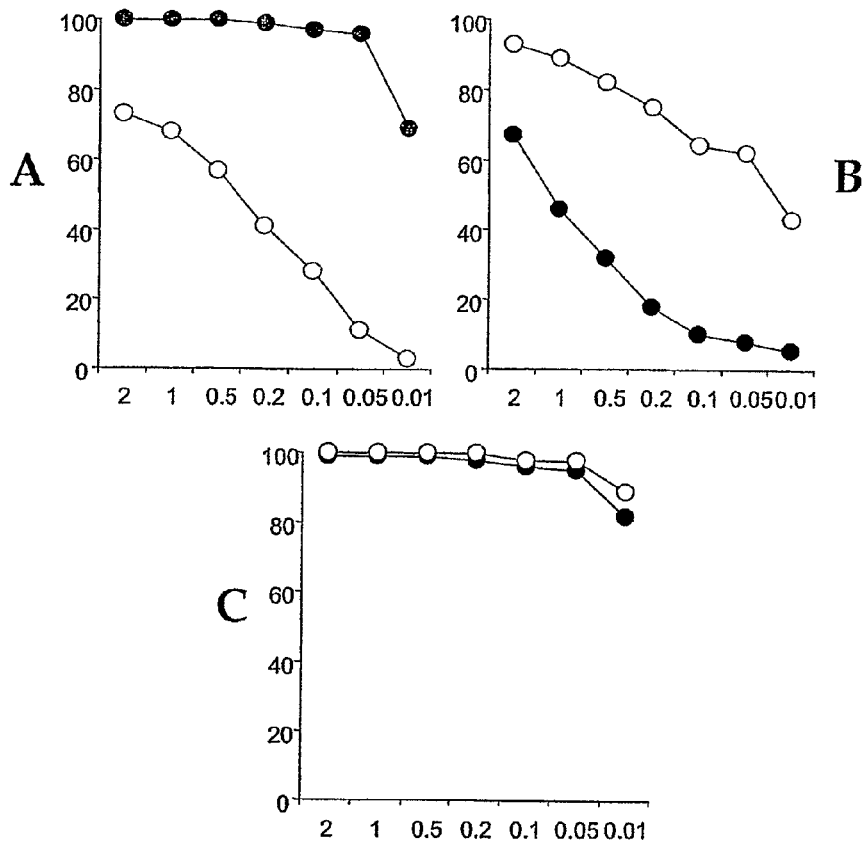
FIG. 4 shows the results of experiments to determine the inhibition of mAb binding to GG-Zym by β-glucan compounds with distinct molecular structures. The y-axes shows % inhibition of ELISA reactivity. The x-axes show the concentration of free inhibitor (mg/ml). Open circles show IgM control mAb; closed circles show 2G8 IgG mAb. The free-phase inhibitors are: (A) laminarin; (B) pustulin; and (C) β-glucan from *S. cerevisiae*.

The experiments indicated that both mAbs showed a significantly reduced binding to GG-Zym in the presence of high doses of either pustulan (β-1,6 glucan) or laminarin (β-1,3 glucan), confirming their basic ability to recognize glucan antigens of any conformation (FIG. 4). On the other hand, on a dose-response basis, the ability of β-1,6 and β-1,3 glucans to compete with mAb binding to GG-Zym greatly differed between the IgM and the IgG mAb, as shown by the opposite profile of inhibition curves in FIG. 4. In fact, ELISA percent inhibitory dose 50 (ID50), i.e. the doses of competitor ligand producing a 50% reduction of O.D. 405 nm values with respect to non-competed mAb readings, were 0.01 and 2.0 mg/ml for laminarin and pustulan, respectively, when used to competitively bind the IgG mAb, whereas they were 2.0 and 0.05 mg/ml when used to competitively bind the control IgM mAb.

8. Ability by IgG and the IgM mAb to Compete for Binding to the Same Antigen

Plastic-bound laminarin or pustulan were reacted with a mixture containing a fixed amount of any of the two mAb and decreasing concentration of its mAb counterpart of different isotype. Binding of IgG or of IgM mAb was revealed by an appropriate secondary reaction with AP-conjugated anti mouse IgG or IgM antibodies.

Figure 5:
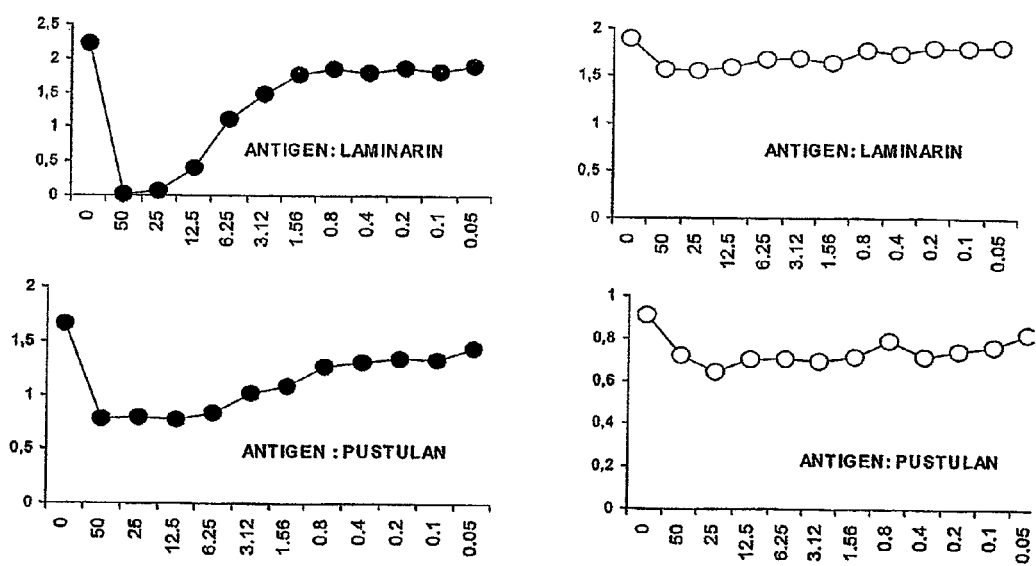
FIG. 5 shows the results of experiments to determine the ability by IgG and the IgM mAb to compete for binding to the same antigen. The y-axes shows binding to plastic-adsorbed antigen (OD 405 nm). The x-axes show the concentration of the competitor mAb (ng/ml). Open circles show the binding of the IgM control mAb in the presence of mAb 2G8; closed circles show the binding of 2G8 IgG mAb in the presence of IgM control mAb.

FIG. 5 shows the O.D. 405 readings generated by each mAb in the absence (empty symbols) or in the presence (full symbols) of different doses of counterpart mAb. The control IgM mAb demonstrated a pronounced ability to displace the IgG mAb not only upon reaction with pustulan, the antigenic substrate to which it has a greater affinity but even upon reaction with laminarin, an antigen for which it has a reduced affinity.

9. Expression of mAb 2G8 and IgM Control mAb Epitopes on *C. albicans* Cells

Untreated, live yeast cells (a, e) or germ-tubes (b, f), yeast cells treated with dithiothreitol and proteinase K (c, g) and purified glucan ghosts from *C. albicans* were spotted onto microscope slides and reacted with mAb 2G8 (a, b, c, d) or control IgM mAbs (e, f, g, h). mAb ligation was revealed with fluorescein isothiocyanate-conjugate anti mouse IgG or IgM antibody (Sigma), and observed with a Leitz Diaplan fluorescence microscopy.

Figure 6:
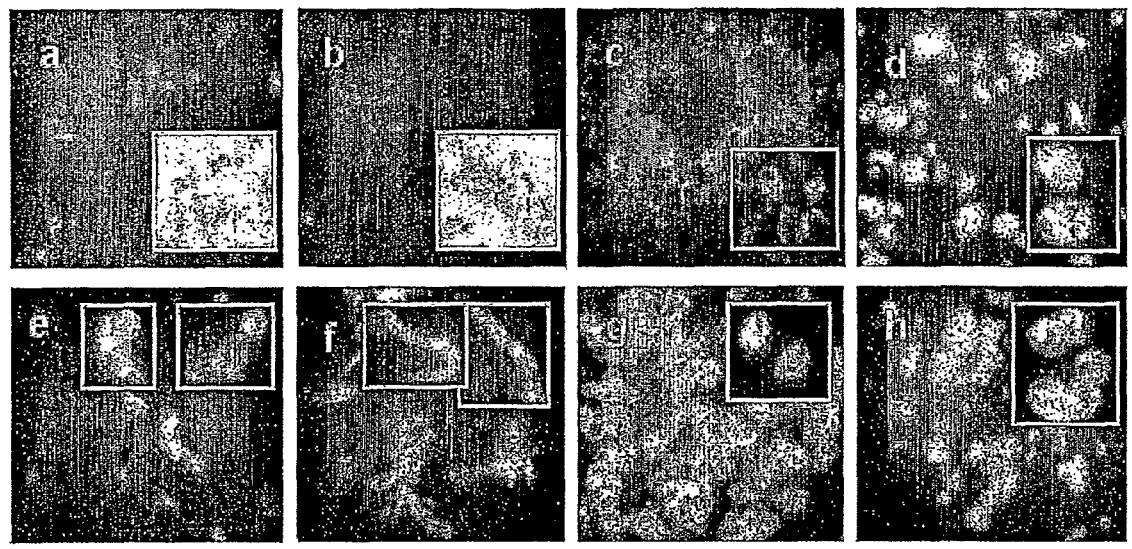
FIG. 6 shows the indirect immunofluorescence localisation of 2G8 and an IgM control glucan epitopes on *C. albicans* cell. The Figure represents the pattern of reactivity observed for the 2G8 and control mAbs in two independent experiments. Inserts in panels a and b show the phase-contrast aspect of the same microscopic field of the corresponding panel. Inserts in panels c, d, e, f, g, h, show details of the immunofluorescence staining patterns. Magnification, ×1000.

Immunofluorescence staining of live, intact yeast or germ-tube cells demonstrated that the mAb 2G8 epitope was not expressed on the cell surface in in vitro cultured *Candida* cells (FIG. 6, a, b). The surface of both yeasts and germ-tube positively reacted with control IgM mAb (FIG. 6, e, f) though not uniformly. Control IgM mAb preferential epitopes were particularly prominent in specific zones of the yeast cells, apparently corresponding to bud scars, and on emerging buds. In germ-tubes, IgM control mAb appeared to stain with a particular intensity the primary septum between mother yeast cell and the protruding hyphal filament, and particular areas of the hyphal filament itself (FIG. 6, e, f and relative inserts). The treatment with dithiothreitol and proteinase K, which is known to remove the superficial, mannoproteic, cell wall layer, rendered yeast cells uniformly reactive with control IgM mAb and also exposed some mAb 2G8-reactive cell wall components (FIG. 6, c, g). Both mAbs demonstrated a strong and comparably intense reactivity with purified glucan ghosts, i.e. cells deprived of soluble outer and inner cell wall and cytoplasmic components by strong hot alkali and acid extraction (FIG. 6, d,h).

It can be concluded that mAb 2G8 preferentially recognised constituents confined in the inner cell wall layers, whereas control IgM mAb preferentially recognised epitopes that span the entire cell wall. This is consistent with the proposed differential preferences of the mAbs for β-1,3 and β-1,6 glucan and with the current knowledge on the fine structural organisation of the yeast cell wall [63]. In particular, the finding that control IgM mAb-preferred, β-1,6 glucan epitopes are surface expressed is in line with the notion that a β-1,6-linked glucan moiety is tightly interconnected with the superficial capsule-like mannoprotein layer of *Candida* cell wall [63].

10. 2G8, But not Control IgM Anti-Glucan mAb can Protect Against Disseminated Experimental Candidiasis It has been suggested that anti β-glucan antibodies may significantly contribute to the protection against disseminated *Candida* infections which is induced by vaccination with glucan-exposing *Candida* cells [59]. The anti-glucan mAbs of the present invention were assayed in a murine model of disseminated candidiasis.

CD2F1 mice were given a single i.p. administration (0.5 ml) of 2G8 or control IgM purified mAb preparations of equivalent anti-glucan titers and protein content, followed, 2 hours later, by a sublethal i.v. challenge with *C. albicans*.

In A, groups of three mice were injected i.p. with 0.5 ml of purified preparations of mAb 2G8 or control IgM, or with PBS only (Contr). In B, mice were given 0.25 ml of each mAb diluted with 0.25 ml PBS, or a mixture of the two (0.5 ml total). Animals were challenged i.v. 2 hours later with $5\times10^5$ cells of *C. albicans*.

Figure 7:
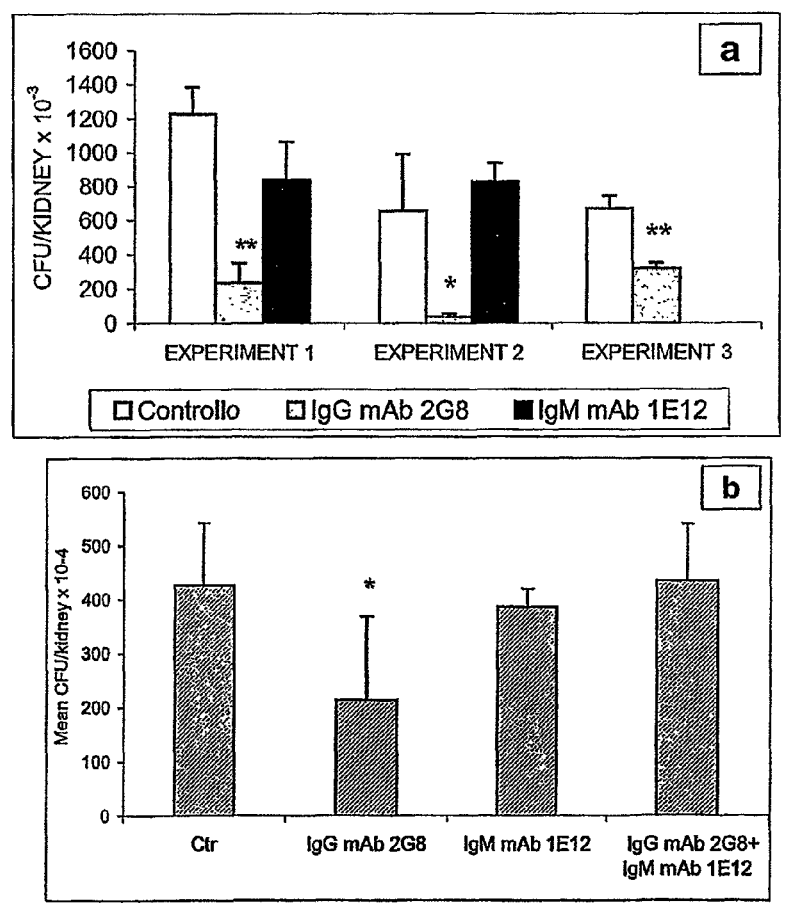
FIG. 7 shows the fungal burden in the kidney of CD2F1 mice following i.p. administration of 2G8 and IgM control mAbs in a murine experimental model of disseminated candidiasis.

Two days after challenge, the animals were sacrificed and the fungal burden in the kidney was evaluated by a classical CFU enumeration to determine protection in comparison with control, PBS-treated mice. The results from the three independent experiments are shown in FIG. 7, panel a. Data represent weighted means+SE of CFU counts measured for each group. The asterisks indicate a statistically significant difference (*$P<0.05$ and **$P<0.001$) with respect to the control group (two-tailed Student's t test).

Despite the well-known and expected variability of these in vivo experiments, and the use of a single mAb administration, it was found that animals receiving mAb 2G8 had significantly fewer fungal cells in their kidneys than animals receiving control IgM mAb or control animals treated with buffer only. In one experiment, *Candida* colonisation of the mouse kidney was substantially negated by the mAb treatment. Interestingly, control IgM mAb was completely ineffective in contrasting fungal invasion, as treated mice always showed CFU counts in their kidneys which were comparable or even higher than those measured in the control group.

In another experiment, the animals received both mAbs, at half strength, and the protective ability was compared with single, half strength mAb (FIG. 7, panel b). Interestingly, the control IgM mAb was not only incapable of conferring protection by itself but was also capable of negating the protection conferred by the anti beta-1-3 mAb. This is in line with the supposed role of blocking antibodies for some anti-cell surface specificities as suggested in reference 64.

Figure 8:
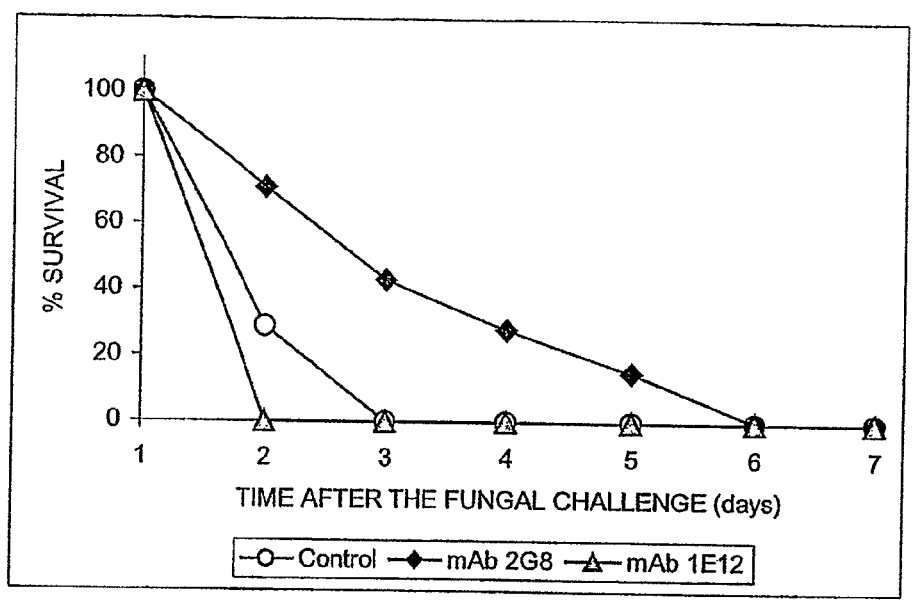
FIG. 8 shows the percent survival at the indicated times of mice administered a single dose of β-glucan mAbs following a lethal i.v. challenge with *C. albicans*.

To further investigate the protective activity exerted by 2G8 mAb, survival of mAb-treated mice following a lethal fungal challenge was also monitored. In a preliminary experiment (FIG. 8), mice (7 per group) received i.p the same dose of purified mAbs as in experiments of FIG. 7 *a*, or PBS only (Control). Two hours later, the animals were challenged i.v. with $10^6$ cells of *C. albicans*. A single i.p. injection of mAb 2G8 2 hours before challenge significantly prolonged mice survival, in contrast with the complete lack of protective effect by control IgM mAb.

11. 2G8 Binds to *Aspergillus* and *Candida* and Inhibits Fungal Growth

Figure 9:
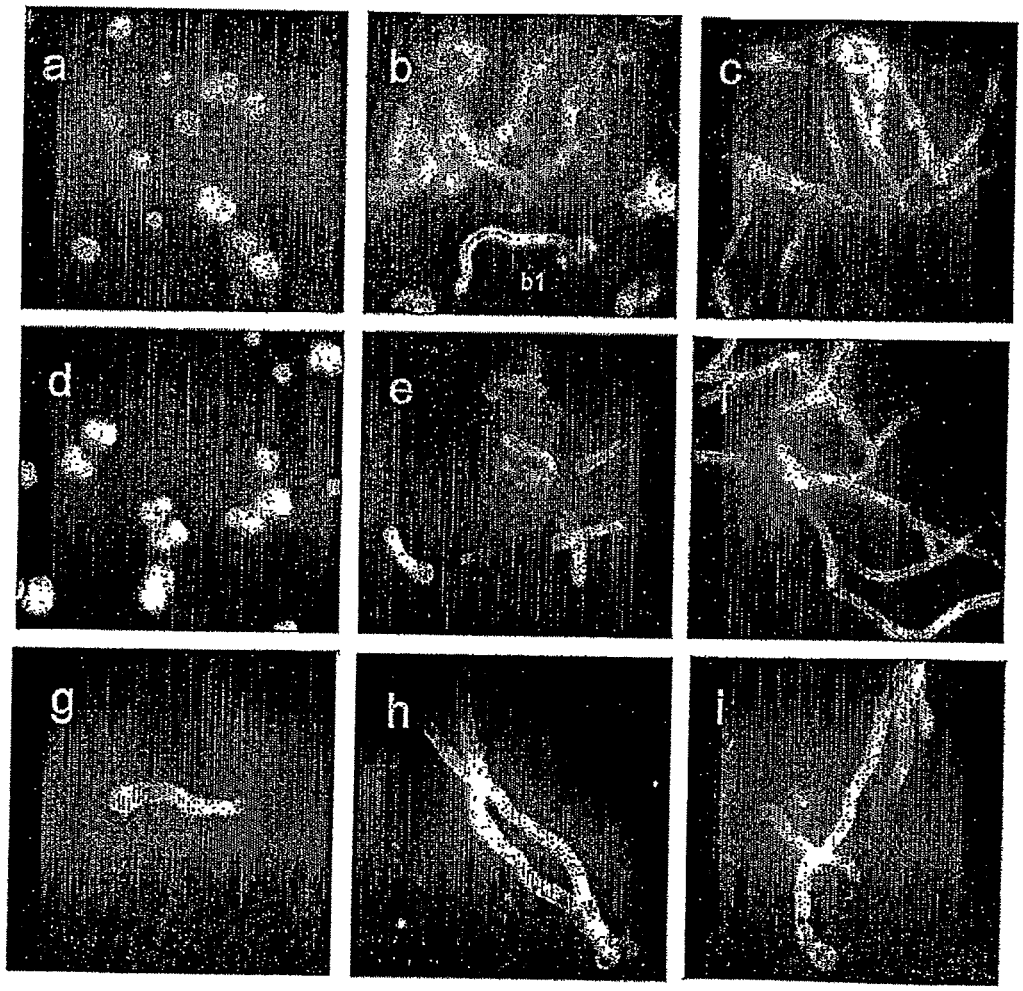
FIG. 9 shows indirect immunofluorescence staining of: (a,d) isolated *C. albicans* β-glucan cell wall ghosts; (b,e) *C. albicans* germ-tubes; (c,f) hyphal filaments of *C. albicans*; (g) germinated conidium of *A. fumigatus*; (h,i) *A. fumigatus* hyphae.

Anti-laminarin serum and the 2G8 mAb were used for immunofluorescence staining of (i) isolated β-glucan cell wall ghosts of *C. albicans*; (ii) *C. albicans* germ tubes; (iii) hyphal filaments of *C. albicans*; (iv) germinated conidium of *A. fumigatus*; and (v) *A. fumigatus* hyphae. Results are shown in FIG. 9. Panels (a), (b), (c), (g) and (h) show results using the anti-laminarin serum; panels (d), (e), (f) and (i) show results using 2G8. Thus both of the antibody preparations bind to all of the fungal samples.

Moreover, in vitro growth of *C. albicans* and *A. fumigatus* is significantly restricted by the anti-β-glucan antibodies, and Lam-CRM vaccination significantly prolongs the survival of mice subjected to a systemic challenge with *A. fumigatus*.

Figure 10:
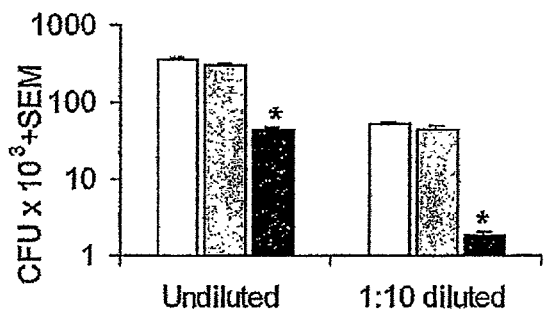
FIG. 10 shows CFR numbers after growth of *C. albicans* in the presence of serum raised against: (white) adjuvant alone; (grey) CRM carrier alone; or (black) Laminarin.

FIG. 10 shows the number of CFU in *C. albicans* cultures grown overnight in the presence of whole or 1:10 diluted anti-Lam-CRM or control sera, and the anti-glucan serum significantly reduces growth compared to controls.

Figure 11:
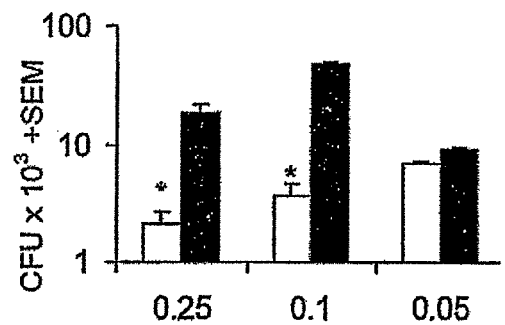
FIG. 11 shows CFU reduction after growth with 0.25, 0.1 or 0.05 mg/ml of (white) 2G8 or (black) anti-CRM monoclonal antibody.

FIG. 11 shows the dose-response of *C. albicans* CFU reduction by the 2G8 mAb or by a control anti-CRM mAb. 2G8 shows significantly better CFU reduction at 0.25 and 0.1 mg/ml.

Figure 12:
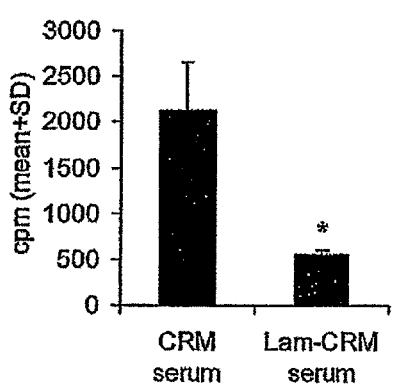
FIG. 12 shows the effect of anti-Lam-CRM or control anti-CRM serum on the in vitro growth of *A. fumigatus*, as evaluated by $^3$H-glucose incorporation assays.

FIG. 12 shows the effect of anti-Lam-CRM and control anti-CRM serum on the in vitro growth of *A. fumigatus*, as evaluated by $^3$H-glucose incorporation assays.

Figure 13:
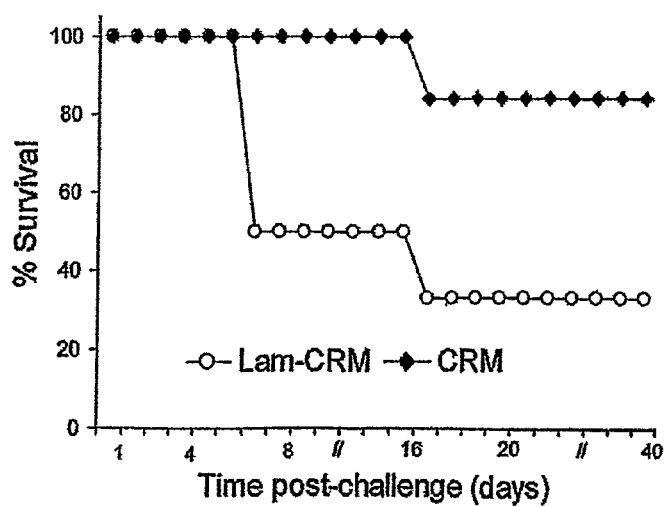
FIG. 13 shows the numbers of mice surviving intravenous challenge with *A. fumigatus* after being immunised wither with the Lam-CRM conjugate or with CRM.

FIG. 13 shows the numbers of mice surviving intravenous challenge with *A. fumigatus* after being immunised wither with the Lam-CRM conjugate or with CRM.

It will be understood that the invention has been described by way of example only and modifications may be made whilst remaining within the scope and spirit of the invention.

REFERENCES

The Contents of which are Hereby Incorporated by Reference

[1] Deepe (1997) *Clin. Microbiol. Rev.* 10:585-596.
[2] Polonelli et al. (2000) *Med Mycol* 38 Suppl 1:281-292.
[3] Casadevall (1995) *Infect. Immun.* 63:4211-4218.
[4] Cassone (2000) *Nippon Ishinkin Gakkai Zasshi* 41(4): 219.
[5] U.S. Pat. No. 5,578,309 (see also WO95/31998).
[6] U.S. Pat. No. 6,309,642 (see also WO98/23287).
[7] WO01/51517
[8] WO03/097091
[9] Kabat et al., 1987, in Sequences of Proteins of Immunological Interest, US Department of Health and Human Services, NIH, USA
[10] Breedveld (2000) *Lancet* 355(9205):735-740.
[11] Gorman & Clark (1990) *Semin. Immunol.* 2:457-466
[12] Jones et al. *Nature* 321:522-525 (1986)
[13] Morrison et al., *Proc. Natl. Acad. Sci, U.S.A.,* 81:6851-6855 (1984)
[14] Morrison & Oi, *Adv. Immunol.,* 44:65-92 (1988)
[15] Verhoeyer et al., *Science* 239:1534-1536 (1988)
[16] Padlan, *Molec. Immun.* 28:489-498 (1991)
[17] Padlan, *Molec. Immunol.* 31(3):169-217 (1994).
[18] Kettleborough et al., *Protein Eng.* 4(7):773-83 (1991).
[19] WO 98/24893
[20] WO 91/10741
[21] WO 96/30498
[22] WO 94/02602
[23] U.S. Pat. No. 5,939,598.
[24] Conrath et al. (2003) *Dev Comp Immunol* 27:87-103.
[25] Muyldermans (2001) *J Biotechnol* 74:277-302.
[26] Huston et al. (1988) *Proc. Nat. Acad. Sci. USA* 85:5879-5883.
[27] U.S. Pat. No. 5,091,513
[28] U.S. Pat. No. 5,132,405
[29] U.S. Pat. No. 4,946,778
[30] Pack et al., (1992) *Biochem* 31:1579-1584
[31] Cumber et al. (1992) *J. Immunology* 149B:120-126
[32] Radrizzani M et al., (1999) *Medicina (B Aires)* 59(6): 753-8.
[33] Radrizzani M et al., (2000) *Medicina (B Aires)* 60 Suppl 2:55-60.
[34] U.S. Pat. No. 4,011,308
[35] U.S. Pat. No. 4,722,890
[36] U.S. Pat. No. 4,016,043
[37] U.S. Pat. No. 3,876,504
[38] U.S. Pat. No. 3,770,380
[39] U.S. Pat. No. 4,372,745
[40] Kohler & Milstein (1975) *Nature* 256:495-497
[41] *Kuby Immunology* (4th edition, 2000; ASIN: 0716733315
[42] Jones et al. *Biotechnol Prog* 2003, 19(1):163-8
[43] Cho et al. *Cytotechnology* 2001, 37:23-30
[44] Cho et al. *Biotechnol Prog* 2003, 19:229-32
[45] U.S. Pat. No. 5,807,715
[46] U.S. Pat. No. 6,300,104
[47] Inbar et al. (1972) *Proc. Nat. Acad. Sci USA* 69:2659-2662
[48] Hochman et al. (1976) *Biochem* 15:2706-2710
[49] Ehrlich et al. (1980) *Biochem* 19:4091-4096
[50] Siegel, *Transfus. Clin. Biol.* (2002) 9(1): 15-22;
[51] Sidhu, *Curr. Opin. Biotechnol.* (2000) 11(6):610-616;
[52] Sharon, et al., *Comb. Chem. High Throughput Screen* (2000) 3(3): 185-196;
[53] Schmitz et al., *Placenta*, (2000) 21 SupplA: S106-12
[54] Reiss E. et al., (2000) *Med Mycol.* 38 Suppl 1:147-159
[55] Gennaro (2000) *Remington: The Science and Practice of Pharmacy.* 20th ed., ISBN: 0683306472
[56] Almeida & Alpar (1996) *J. Drug Targeting* 3:455-467.
[57] Wills et al. (2000) *Emerging Therapeutic Targets* 4:1-32.
[58] Malavasi et al., J. Med. Microbiol. 1988 December; 27(4):233-8.
[59] Bromuro et al., Infect Immun. 2002 October; 70(10): 5462-70
[60] Cassone et al. (1988) J. Med Microbiol December; 27(4):233-238
[61] Torosantucci et al. J Leukoc Biol. 2000 68(6):923-32
[62] Kapteyn et al., (1999) Biochim. Biophys. Acta 1426: 373-393
[63] Klis at al, (2001) Med Mycol. 39 Suppl 1:1-8.
[64] Bromuro et al. (2002) *Infect Immun* 70(10):5462-70.

The invention claimed is:

1. A method of inhibiting growth and/or survival of a microbial pathogen in a patient, wherein said microbial pathogen is *Candida albicans* or *Aspergillus fumigatus* and has a cell wall containing β-1,3-glucan and β-1,6-glucan, said method comprising administering to the patient a composition comprising a monoclonal antibody that shows preferential binding to a β-1,3-glucan over a β-1,6-glucan, wherein the antibody is a human antibody, a chimeric antibody, a humanized antibody, a single chain antibody or a functional fragment thereof, and further wherein the antibody comprises heavy chain variable CDRs comprising the amino acid sequences of SEQ ID NOs: 4, 6, and 8, and light chain variable CDRs comprising the amino acid sequences of SEQ ID NOs: 10, 12 and 14.

2. The method of claim 1, wherein the antibody has a light chain variable sequence of SEQ ID NO: 1 and a heavy chain variable sequence of SEQ ID NO:2.

3. The method of claim 1, wherein the antibody is a human or humanized antibody or is a chimeric antibody.

4. The method of claim 1, wherein the antibody is a single chain antibody.

5. The method of claim 1, wherein the antibody has microbicidal activity against the microbial pathogen.

6. The method of claim 5, wherein the microbial pathogen is *C. albicans*.

7. The method of claim 5, wherein the microbe is *A. fumigatus*.

8. The method of claim 6 wherein the patient is protected against candidiasis.

9. The method of claim 1, wherein the composition further comprises an anti-fungal agent.

* * * * *